United States Patent [19]

Ikegawa et al.

[11] Patent Number: 5,798,357
[45] Date of Patent: Aug. 25, 1998

[54] AGENT FOR PROPHYLAXIS AND TREATMENT OF THROMBOXANE $A_2$-MEDIATED DISEASES

[75] Inventors: Ruriko Ikegawa; Teruaki Imada; Norifumi Nakamura, all of Hirakata; Keizo Tanikawa, Funabashi; Nobutomo Tsuruzoe, Minamisaitama-gun, all of Japan

[73] Assignees: The Green Cross Corporation, Osaka; Nissan Chemical Industries, Ltd., Tokyo, both of Japan

[21] Appl. No.: 687,604

[22] PCT Filed: Feb. 20, 1995

[86] PCT No.: PCT/JP95/00244

§ 371 Date: Aug. 8, 1996

§ 102(e) Date: Aug. 8, 1996

[87] PCT Pub. No.: WO95/22329

PCT Pub. Date: Aug. 24, 1995

[30] Foreign Application Priority Data

Feb. 22, 1994 [JP] Japan .................. 6-024556

[51] Int. Cl.⁶ .................................. A61K 31/495
[52] U.S. Cl. .................................. 514/252
[58] Field of Search .............................. 514/252

[56] References Cited

FOREIGN PATENT DOCUMENTS 0 482 208  4/1992  European Pat. Off. .

*Primary Examiner*—Raymond Henley, III
*Attorney, Agent, or Firm*—Sughrue, Mion, Zinn, Macpeak & Seas, PLLC

[57] ABSTRACT

An agent for the prophylaxis or treatment of $TXA_2$-mediated diseases, particularly, a $TXA_2$ synthetase inhibitor, which comprises a pyridazinone compound of the formula (I)

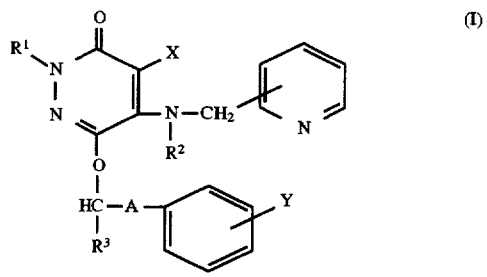

wherein each symbol is as defined in the specification, or a pharmacologically acceptable salt thereof as an active ingredient. The pyridazinone compound (I) and pharmacologically acceptable salts thereof used in the present invention have prophylactic and therapeutic activities against $TXA_2$-mediated diseases, particularly a $TXA_2$ synthetase inhibitory action and are useful as an agent for the prophylaxis or treatment of $TXA_2$-mediated diseases, particularly as $TXA_2$ synthetase inhibitors.

6 Claims, No Drawings

AGENT FOR PROPHYLAXIS AND TREATMENT OF THROMBOXANE $A_2$-MEDIATED DISEASES

This application is a 571 of PCT/JP95/00244 filed Feb. 20, 1995.

1. Technical Field

The present invention relates to an agent for the prophylaxis and treatment of thromboxane $A_2$-mediated diseases, which comprises a pyridazinone compound or a pharmacologically acceptable salt thereof as an active ingredient, particularly to a thromboxane $A_2$ synthetase inhibitor.

2. Background Art

Thromboxane $A_2$ ($TXA_2$) is mainly produced and released from platelets, and shows strong platelet aggregating action and vasopressing action. There are many reports with regard to the pathophysiological role thereof. The production of $TXA_2$ has been found to be accelerated in the diseases such as arteriosclerosis, diabetes, ischemic heart diseases, pulmonary diseases, hypertension, shock, Kawasaki disease and alcoholic liver disease, thus indicating a high probability of $TXA_2$ being involved in the onset and aggravation of these diseases. For the improvement of these diseases, $TXA_2$ synthetase inhibitors and $TXA_2$ antagonists such as imidazole derivatives, pyridine derivatives and imidazopyridine derivatives have been developed. However, an agent for the prophylaxis and treatment of $TXA_2$-mediated diseases, which has more superior effects, has beed desired.

It has been already known that pyridazinone compounds have platelet aggregation inhibitory action, cardiotonic action, vasodilating action and anti-SRS-A (Slow Reacting Substances of Anaphylaxis) action (WO91/16314, U.S. Pat. No. 5,202,323, EP-A-482208).

DISCLOSURE OF THE INVENTION

It has now been found that said pyridazinone compounds and pharmacologically acceptable salts thereof have an action heretofore not known, namely, prophylactic and therapeutic activities against $TXA_2$-mediated diseases, particularly, $TXA_2$ synthetase inhibitory action.

It is therefore an object of the present invention to provide an agent for the prophylaxis and treatment of $TXA_2$-mediated diseases, by using a pyridazinone compound, particularly a $TXA_2$ synthetase inhibitor.

According to the present invention, there is provided an agent for the prophylaxis or treatment of $TXA_2$-mediated diseases, particularly a $TXA_2$ synthetase inhibitor, which comprises, as an active ingredient, a pyridazinone compound of the formula (I)

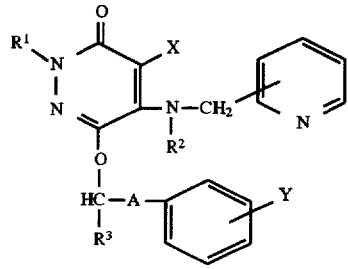

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom and A is a $C_1$–$C_8$ alkylene optionally substituted by hydroxyl, or a pharmacologically acceptable salt thereof.

The symbols used in the present specification are explained in the following.

The lower alkyl for $R^1$, $R^2$ and $R^3$ may be linear or branched and has 1 to 6 carbon atoms, such as methyl, ethyl, n-propyl, isopropyl, n-butyl, isobutyl, sec-butyl, t-butyl, pentyl and hexyl.

Preferable $R^1$ and $R^2$ are each hydrogen atom, and preferable $R^3$ is hydrogen atom or $C_1$–$C_4$ alkyl.

The $C_1$–$C_4$ alkyl for $R^3$ is exemplified by methyl, ethyl, n-propyl, isopropyl, n-butyl, isobutyl, sec-butyl and t-butyl.

The halogen atom for X and Y is, for example, fluoro atom, chloro atom, bromo atom or iodo atom, with preference given to halogen atom for X, and halogen atom or hydrogen atom for Y.

The $C_1$–$C_8$ alkylene for A, which is optionally substituted by hydroxyl, may be linear or branched and is exemplified by methylene, ethylene, propylene, butylene, pentylene, hexylene, heptylene, octylene, 2,2-dimethylethylene, 2,2-diethylethylene, 2,2-di-n-propylethylene, hydroxymethylene, 1-hydroxyethylene, 2-hydroxyethylene and 3-hydroxypropylene. Preferred is $C_1$–$C_5$ alkylene optionally substituted by hydroxyl.

In the formula (I), the bonding site of methylene and pyridine ring is not particularly limited. Preferable site is the 3-position relative to the nitrogen atom on the pyridine ring.

Y may be substituted at any position on the benzene ring, with preference given to the 4-position.

In particular, a pyridazinone compound wherein, in the formula (I), $R^1$ and $R^2$ are hydrogen atoms, $R^3$ is a hydrogen atom or a $C_1$–$C_4$ alkyl, X is a halogen atom, Y is a halogen atom or hydrogen atom and A is a $C_1$–$C_5$ alkylene optionally substituted by hydroxyl is preferable.

Examples of more preferable pyridazinone compound (I) include 4-bromo-6-(3-phenylpropoxy)-5-(3-pyridylmethylamino)-3(2H)-pyridazinone, 4-chloro-6-(3-phenylpropoxy)-5-(3-pyridylmethylamino)-3(2H)-pyridazinone, 4-chloro-6-[3-(4-chlorophenyl)propoxy]-5-(3-pyridylmethylamino)-3(2H)-pyridazinone, 4-bromo-6-[3-(4-chlorophenyl)propoxy]-5-(3-pyridylmethylamino)-3(2H)-pyridazinone, 4-bromo-6-(2,2-dimethyl-3-phenylpropoxy)-5-(3-pyridylmethylamino)-3(2H)-pyridazinone, 4-chloro-6-(2,2-dimethyl-3-phenylpropoxy)-5-(3-pyridylmethylamino)-3(2H)-pyridazinone, 4-bromo-6-[3-(4-chlorophenyl)-2,2-dimethylpropoxy]-5-(3-pyridylmethylamino)-3(2H)-pyridazinone, 4-chloro-6-[3-(4-chlorophenyl)-2,2-dimethylpropoxy]-5-(3-pyridylmethylamino)-3(2H)-pyridazinone, 4-bromo-6-[3-(4-chlorophenyl)-3-hydroxypropoxy]-5-(3-pyridylmethylamino)-3(2H)-pyridazinone, 4-chloro-6-[3-(4-chlorophenyl)-3-hydroxypropoxy]-5-(3-pyridylmethylamino)-3(2H)-pyridazinone, 4-bromo-6-[3-(4-chlorophenyl)-2-hydroxypropoxy]-5-(3-pyridylmethylamino)-3(2H)-pyridazinone and 4-chloro-6-[3-(4-chlorophenyl)-2-hydroxypropoxy]-5-(3-pyridylmethylamino)-3(2H)-pyridazinone.

The pyridazinone compound (I) used in the present invention includes stereo and optical isomers.

The pyridazinone compound (I) is a known compound and can be produced by a method described in, for example, WO91/16314, U.S. Pat. No. 5,202,323, EP-A-482208 and International Patent Application No. PCT/JP95/69.

The pharmacologically acceptable salts of the pyridazinone compound (I) are, for example, salts with inorganic acid (e.g. hydrochloride, hydrobromide, phosphate and sulfate) and salts with organic acid (acetate, succinate, maleate, fumarate, malate and tartrate).

The pyridazinone compound (I) can be converted to the aforementioned salts by a known method.

The method for confirming the action of the compound (I) used in the present invention is subject to no particular limitation and the action can be confirmed by a known method.

The pyridazinone compound (I) and pharmacologically acceptable salts thereof, which are the active ingredients in the present invention, are extremely low toxic and have prophylactic and therapeutic activities against $TXA_2$-mediated diseases, particularly a $TXA_2$ synthetase inhibitory action, in mammals such as human, dog, cow, horse, rabbit, mouse and rat. That is, they have prophylactic and therapeutic effects against $TXA_2$-mediated diseases, such as cerebral infarction, cerebral thrombosis, bronchial asthma, cerebral stroke, myocardial infarction, acute heart failure, angina pectoris, hypertension, arteriosclerosis obliterans, thromboangiitis obliterans, diabetic nephropathy, diabetic neuropathy and hypertriglyceridemia caused by diabetes.

The dosage form of the pyridazinone compound (I) and pharmacologically acceptable salts thereof is exemplified by non-oral administration of, for example, injection (subcutaneous, intravenous, intramuscular, intraperitoneal injections), ointment, suppository or aerosol, and oral administration of, for example, tablet, capsule, granule, pill, syrup, liquid, emulsion or suspension.

The pyridazinone compound (I) and pharmacologically acceptable salts thereof are formulated into preparations by a method conventionally used for manufacturing pharmaceuticals.

The tablet, capsule, granule and pill for oral administration are prepared by using, for example, excipient (e.g. sucrose, lactose, glucose, starch and mannit), binder (e.g. syrup, gum arabic, gelatin, sorbit, tragacanth, methylcellulose and polyvinylpyrrolidone), disintegrator (e.g. starch, carboxymethylcellulose or calcium salt thereof, microcrystalline cellulose and polyethylene glycol) and lubricant (e.g. talc, magnesium stearate, calcium stearate, silica, sodium laurate and glycerol).

The injection, aerosole, syrup, liquid, emulsion and suspension are prepared using solvents for the active ingredient (e.g. water, ethyl alcohol, isopropyl alcohol, propylene glycol, 1,3-butylene glycol and polyethylene glycol), surfactant (e.g. sorbitan fatty acid ester, polyoxyethylenesorbitan fatty acid ester, polyoxyethylene fatty acid ester, polyoxyethylene ether of hydrogenated castor oil and lecithin), suspending agent (e.g. cellulose derivative such as methylcellulose and sodium salt of carboxymethylcellulose, and natural rubber such as tragacanth and gum arabic), preservative (e.g. p-hydroxybenzoate, benzalkonium chloride and sorbic acid salt) and the like. Suppositories are prepared using, for example, polyethylene glycol, lanolin and coconut oil.

The dose of the pyridazinone compound (I) and pharmacologically acceptable salts thereof is appropriately determined according to age, body weight, severity of symptom and the like of patients, and they are generally administered in 0.001–500 mg/day, preferably 0.005–100 mg/day in a single to several times divided doses to a human adult.

The present invention is explained in more detail by way of Examples and Experimental Examples. It should be understood that they do not limit the present invention in any way.

The following experiments were performed using the following drugs and the like.

Compound A, 4-bromo-6-[3-(4-chlorophenyl)propoxy]-5-(3-pyridylmethylamino)-3(2H)-pyridazinone hydrochloride, Compound B, 4-bromo-6-|(3S)-(4-chlorophenyl)-3-hydroxypropoxy]-5-(3-pyridylmethylamino)-3(2H)-pyridazinone hydrochloride, and Compound C, 4-bromo-6-|(3R)-(4-chlorophenyl)-3-hydroxypropoxy|-5-(3-pyridylmethylamino)-3(2H)-pyridazinone hydrochloride, which were prepared by conventional methods, were dissolved in 100% dimethyl sulfoxide (DMSO) and used as reagents on dilution with DMSO when in use.

Indomethacin (manufactured by Sigma Chemical Co.) was suspended in physiological saline and a 2.5% sodium carbonate solution (pH ca. 8.0) was dropwise added to dissolve it. Collagen (Collagen Reagent Horm; manufactured by Niko Bioscience) was diluted with a single purpose diluent when in use. With regard to prostaglandin $H_2$ ($PGH_2$; manufactured by Funakoshi), it was re-dissolved in ethanol when in use, after removal of acetone under an $N_2$ gas atmosphere.

Experimental Example 1

$TXA_2$ release from rabbit platelets

Blood was taken from the carotid artery of normal rabbit using ethylenediaminetetraacetic acid (EDTA; 77 mM EDTA, 1/10 vol). The blood was centrifuged at 1800 rpm for 8 minutes and platelet rich plasma in the supernatant was recovered, which was then centrifuged at 3200 rpm for 8 minutes. The sediment (platelet) was washed with Tyrode-HEPES-EDTA buffer and centrifuged at 3200 rpm for 8 minutes. The sediment was suspended in Tyrode-HEPES buffer to prepare washed platelets ($5 \times 10^8$ platelets/ml).

100% DMSO or a reagent (Compound A, 1.5 µl) was added to the washed platelets (270 µl) and the mixture was heated at 37° C. for 2 minutes. Then, collagen (10 µg/ml) and 1 mM $Ca^{2+}$ (or 1 mM $Ca^{2+}$ alone when investigating release from unstimulated platelets) were added and the experiment was started. After heating at 37° C. for 8 minutes, $10^{-3}$M indomethacin was added and the cuvette was placed in ice to stop the reaction. After centrifugation at 10,000 rpm for 10 minutes, the supernatant was taken and stored at −20° C. until used for the $TXA_2$ determination.

Experimental Example 2

Inhibition of $TXA_2$ synthetase using rabbit platelet microsome

Blood was taken from the carotid artery of normal rabbit, using EDTA (77 mM EDTA, 1/10 vol). The blood was centrifuged at 1300 rpm for 10 minutes and platelet rich plasma in the supernatant was recovered, which was centrifuged at 3400 rpm for 15 minutes. The sediment was washed with physiological saline (original volume) and centrifuged at 3400 rpm for 15 minutes. Then, 0.05M Tris-HCl buffer (1 mM EDTA, pH 7.5, 3-fold weight of the wet weight of platelets) was added to the sediment and the mixture was homogenated (2 minutes, full speed) using polytron. The homogenate was centrifuged at 8300 rpm for 15 minutes (Tomy RD-20III, No. 3N) and the supernatant was centrifuged at 1,000,000 rpm for 1 hour (Beckman TL-100, TLA100.3). The sediment was suspended in 0.05M Tris-HCl buffer (1 mM EDTA, pH 7.5, one-third weight of the wet weight of platelets) to prepare a microsomal fraction. The fraction was stored at −80° C. until used for the experiment.

0.05M Tris-HCl buffer (pH 7.5, 890 µl), 100 µl of the above-mentioned microsome (85 µg protein) and 100% DMSO or the reagent (Compound A, 5 µl) were added and the mixture was preincubated at 22° C. for 3 minutes. Then, $PGH_2$ (5 nmol, 5 µl) was added to start the reaction. After incubation at 22° C. for 3 minutes, 1N hydrochloric acid (50 µl) was added to terminate the reaction. 1M Tris base (55 µl) was added to neutralize the reaction mixture and the mixture was centrifuged at 10,000 rpm for 5 minutes. The supernatant was recovered and stored at -20° C. until used for the $TXA_2$ measurement.

The $TXA_2$ amount in the above Experimental Examples was measured as $TXB_2$ (stable compound thereof) amount by the EIA method using $TXB_2$ assay kit (manufactured by Amersham).

The results of Experimental Examples 1 and 2 are shown in Table 1.

TABLE 1

| | $TXA_2$ release suppressing action *1 | | $TXA_2$ synthetase inhibitory action *2 |
|---|---|---|---|
| | stimulated with collagen | not stimulated | |
| Compound A | 0.009 | 1.0 | 0.018 |

Note
*1: amount necessary for 50% inhibition of $TXA_2$ release (μM)
*2: amount necessary for 50% inhibition of $TXA_2$ synthesis (μM)

Experimental Example 3
inhibition of $TXA_2$ synthetase by the use of human platelet microsome In the same manner as in Experimental Example 2 except that human platelet microsome was used instead of rabbit platelet microsome, the experiment was performed. Compound A, Compound B and Compound C were used as reagents.

As a result, $IC_{50}$ (amount necessary to inhibit 50% of $TXA_2$ synthesis) of $TXA_2$ synthetase inhibitory action, when human platelet microsome was used, was 0.010 μM for Compound A, and 0.020 μM and 0.030 μM for Compound B and Compound C as optical isomers, respectively.

Experimental Example 4
acute toxicity

Compound A was orally administered to rats and dogs, and $LD_{50}$ was found to be not less than 2 g/kg, thus demonstrating the extremely low toxicity of the compound (I) used in the present invention.

From the above experimental results, it is evident that the pyridazinone compound (I) and a salt thereof have superior $TXA_2$ release suppressive action and $TXA_2$ synthetase inhibitory action, and are markedly low toxic.

Example 1
Tablet

The following ingredients were mixed by a conventional method and prepared into a sugar coated tablet containing 50 mg of the active ingredient per tablet.

| Compound A | 10 g |
|---|---|
| Lactose | 20 g |
| Starch | 5 g |
| Magnesium stearate | 0.1 g |
| Calcium carboxymethylcellulose | 7 g |
| total | 42.1 g |

Example 2
Capsule

The following ingredients were mixed by a conventional method and packed in a gelatin capsule to prepare a capsule containing 50 mg of the active ingredient per capsule.

| Compound A | 10 g |
|---|---|
| Lactose | 20 g |
| Crystalline cellulose | 10 g |
| Magnesium stearate | 1 g |
| total | 41 g |

Example 3

Ointment

The following ingredients were mixed by a conventional method to prepare a 1% ointment.

| Compound A | 1 g |
|---|---|
| Olive oil | 20 g |
| White petrolatum | 79 g |
| total | 100 g |

Example 4

Aerosol suspension

The following ingredients (A) were mixed and the obtained mixture was charged in a container equipped with a valve. A propellant (B) was forced therein at 20° C. from the valve nozzle to about 2.46–2.81 mg/cm² gauge pressure to prepare an aerosol suspension.

| (A) Compound A | 0.25 wt % |
|---|---|
| Isopropyl myristate | 0.10 wt % |
| Ethanol | 26.40 wt % |
| (B) A 60 wt %–40 wt % mixture of 1,2-dichlorotetrafluoroethane and 1-chloropentafluoroethane | 73.25 wt % |

The pyridazinone compound (I) and pharmacologically acceptable salts thereof have prophylactic and therapeutic activities against $TXA_2$-mediated diseases, particularly a $TXA_2$ synthetase inhibitory action, and are useful as agents for the prophylaxis and treatement of $TXA_2$-mediated diseases, particularly as $TXA_2$ synthetase inhibitors. They have prophylaxis and therapeutic effects against $TXA_2$-mediated diseases, such as cerebral infarction, cerebral thrombosis, bronchial asthma, cerebral stroke, myocardial infarction, acute heart failure, angina pectoris, hypertension, arteriosclerosis obliterans, thromboangiitis obliterans, diabetic nephropathy, diabetic neuropathy and hypertriglyceridemia caused by diabetes.

We claim:

1. A method for the prophylaxis or treatment of a disease selected from the group consisting of arteriosclerosis obliterans, diabetic nephropathy, diabetic neuropathy, and hypertriglycleridemia caused by diabetes, comprising administering a pyridazinone compound of the formula (I)

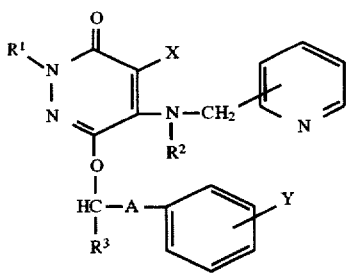

wherein $R^1$, $R^2$ and $R^3$ are each independently a hydrogen atom or a lower alkyl group, X is a halogen atom, a cyano group or a hydrogen atom, Y is a halogen atom, a trifluoromethyl group or a hydrogen atom and A is a $C_1$–$C_8$ alkylene group optionally substituted by a hydroxyl group, or a pharmacologically acceptable salt thereof.

2. The method of claim 1, wherein $R^1$ and $R^2$ are each a hydrogen atom, $R^3$ is a hydrogen atom or a $C_1$–$C_4$ alkyl, X is a halogen group atom, Y is a halogen atom or a hydrogen atom and A is a $C_1$–$C_5$ alkylene group optionally substituted by a hydroxyl group.

3. The method of claim 1, wherein the pyridazinone compound of the formula (I) is a member selected from the group consisting of;
4-bromo-6-(3-phenylpropoxy)-5-(3-pyridylmethylamino)-3(2H)-pyridazinone,
4-chloro-6-(3-phenylpropoxy)-5-(3-pyridylmethylamino)-3(2H)-pyridazinone,
4-chloro-6-[3-(4-chlorophenyl)propoxy]-5-(3-pyridylmethylamino)-3(2H)-pyridazinone,
4-bromo-6-[3-(4-chlorophenyl)propoxy]-5-(3-pyridylmethylamino)-3(2H)-pyridazinone,
4-bromo-6-(2,2-dimethyl-3-phenylpropoxy)-5-(3-pyridylmethylamino)-3(2H)-pyridazinone,
4-chloro-6-(2,2-dimethyl-3-phenylpropoxy)-5-(3-pyridylmethylamino)-3(2H)-pyridazinone,
4-bromo-6-[3-(4-chlorophenyl)-2,2-dimethylpropoxy]-5-(3-pyridylmethylamino)-3(2H)-pyridazinone,
4-chloro-6-[3-(4-chlorophenyl)-2,2-dimethylpropoxy]-5-(3-pyridylmethylamino)-3(2H)-pyridazinone and
4-bromo-6-[3-(4-chlorophenyl)-3-hydroxypropoxy]-5-(3-pyridylmethylamino)-3(2H)-pyridazinone,
4-chloro-6-[3-(4-chlorophenyl)-3-hydroxypropoxy]-5-(3-pyridylmethylamino)-3(2H)-pyridazinone,
4-bromo-6-[3-(4-chlorophenyl)-2-hydroxypropoxy]-5-(3-pyridylmethylamino)-3(2H)-pyridazinone and
4-chloro-6-[3-(4-chlorophenyl)-2-hydroxypropoxy]-5-(3-pyridylmethylamino)-3(2H)-pyridazinone.

4. A method for inhibiting thromboxane $A_2$ synthetase for the prophylaxis or treatment of a disease selected from the group consisting of arteriosclerosis obliterans, diabetic nephropathy, diabetic neuropathy, and hypertriglyceridemia caused by diabetes, in a subject in need thereof comprising administering to said subject an effective amount of a pyridazinone compound of the formula (I)

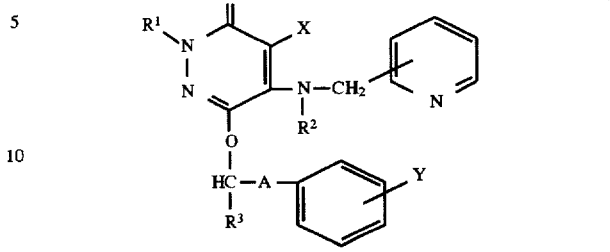

wherein $R^1$, $R^2$ and $R^3$ are each independently a hydrogen atom or a lower alkyl group, X is a halogen atom, a cyano group or a hydrogen atom, Y is a halogen atom, a trifluoromethyl group or a hydrogen atom and A is a $C_1$–$C_8$ alkylene group optionally substituted by a hydroxyl group, or a pharmacologically acceptable salt thereof.

5. The method of claim 4 wherein $R^1$ and $R^2$ are each a hydrogen atom, $R^3$ is a hydrogen atom or a $C_1$–$C_4$ alkyl group, X is a halogen atom, Y is a halogen atom or a hydrogen atom and A is a $C_1$–$C_5$ alkylene group optionally substituted by a hydroxyl group.

6. The method of claim 4 wherein the pyridazinone compound of the formula (I) is a member selected from the group consisting of:
4-bromo-6-(3-phenylpropoxy)-5-(3-pyridylmethylamino)-3(2H)-pyridazinone,
4-chloro-6-(3-phenylpropoxy)-5-(3-pyridylmethylamino)-3(2H)-pyridazinone,
4-chloro-6-[3-(4-chlorophenyl)propoxy]-5-(3-pyridylmethylamino)-3(2H)-pyridazinone,
4-bromo-6-[3-(4-chlorophenyl)propoxy]-5-(3-pyridylmethylamino)-3(2H)-pyridazinone,
4-bromo-6-(2,2-dimethyl-3-phenylpropoxy)-5-(3-pyridylmethylamino)-3(2H)-pyridazinone,
4-chloro-6-(2,2-dimethyl-3-phenylpropoxy)-5-(3-pyridylmethylamino)-3(2H)-pyridazinone,
4-bromo-6-[3-(4-chlorophenyl)-2,2-dimethylpropoxy]-5-(3-pyridylmethylamino)-3(2H)-pyrdazinone,
4-chloro-6-[3-(4-chlorophenyl)-2,2-dimethylpropoxy]-5-(3-pyridylmethylamino)-3(2H)-pyridazinone and
4-bromo-6-[3-(4-chlorophenyl)-3-hydroxypropoxy]-5-(3-pyridylmethylamino)-3(2H)-pyridazinone,
4-chloro-6-[3-(4-chlorophenyl)-3-hydroxypropoxy]-5-(3-pyridylmethylamino)-3(2H)-pyridazinone,
4-bromo-6-[3-(4-chlorophenyl)-2-hydroxypropoxy]-5-(3-pyridylmethylamino)-3(2H)-pyridazinone and
4-chloro-6-[3-(4-chloro phenyl)-2-hydroxypropoxy]-5-(3-pyridylmethylamino)-3(2H)-pyridazinone.

* * * * *